United States Patent [19]
Fechtel et al.

[11] Patent Number: 5,518,588
[45] Date of Patent: May 21, 1996

[54] METHOD FOR PREPARING 3-AMINOPYRIDINES FROM 3-NITROPYRIDINES

[75] Inventors: Ulrich Fechtel; Karlheinz Wembacher; Heinz-Hermann Bokel, all of Darmstadt, Germany

[73] Assignee: Merck Patent Gesellschaft mit beschrankter Haftung, Darmstadt, Germany

[21] Appl. No.: 316,458

[22] Filed: Sep. 30, 1994

[30] Foreign Application Priority Data

Oct. 2, 1993 [DE] Germany .................. 43 33 697.3

[51] Int. Cl.$^6$ ............ C07D 213/73; C07D 213/84; C25B 3/04
[52] U.S. Cl. ............. 205/426; 205/423; 205/436; 205/444; 205/445; 546/112; 546/114; 546/115; 546/118

[58] Field of Search .................. 546/112, 114, 546/115, 118; 204/74; 205/423, 436, 444, 445

[56] References Cited

U.S. PATENT DOCUMENTS

| 5,077,287 | 12/1991 | Ternansky | 514/210 |
| 5,166,209 | 11/1992 | Kelley | 514/300 |
| 5,240,937 | 8/1993 | Kelley | 514/300 |

*Primary Examiner*—Alan L. Rotman
*Attorney, Agent, or Firm*—Millen, White, Zelano, & Branigan

[57] ABSTRACT

The present invention relates to a method for preparing 3-aminopyridines from 3-nitropyridines, in which the nitropyridines are reduced electrochemically in acidic solution.

16 Claims, No Drawings

METHOD FOR PREPARING 3-AMINOPYRIDINES FROM 3-NITROPYRIDINES

SUMMARY OF THE INVENTION

The present invention relates to a method for preparing 3-aminopyridines from 3-nitropyridines, in which the nitropyridines are reduced electrochemically in acidic solution.

According to the novel method, the 3-nitropyridines of the general formula 11 are converted, with reduction of the nitro groups and simultaneous introduction of a group Y, into the 3-amino-Y-pyridines of the general formula 1; in the process, the group Y enters exclusively into the 2-position:

[Structures II → I shown]

The 3-aminopyridines of the formula I are used for the preparation of pharmaceuticals, especially of pyridino [3,4b] azoles which are used as anticonvulsants, e.g., DE 31 486 or DE 41 10 019, or of dihydrodipyridoazepines which can be used as HIV virucides, e.g., EP 0 429 989. It is known to prepare 2-chloro-3,4-diaminopyridine by reduction of 4-amino-3-nitropyridine with tin(II) chloride (e.g., Bremer, Liebigs Ann. Chem. 518 (1934), 274–280). The drawback of this method is primarily the large amounts of tin(IV) salts produced as a waste, which both considerably impair the work-up of the product and also result in serious disposal problems.

As is well known, nitrobenzenes can be converted electrochemically in sulfuric-acid solution, according to the so-called Gattermann reaction, into the corresponding aminophenols, with the simultaneous introduction of a hydroxyl group. There are, however, no indications whatsoever that this electrochemical reduction can also be applied to nitropyridines.

It has now been found that 2-substituted 3-aminopyridines can be prepared advantageously by reducing 3-nitropyridines electrochemically in a solution which contains an acid and, if appropriate, a salt or an alcohol.

The invention therefore relates to a method for preparing 2-Y-3-aminopyridines from the corresponding 3-nitropyridines, with the introduction of the group Y, which involves subjecting the 3-nitropyridine to an electrolytic reduction in the presence of an acid and, if is appropriate, of a salt of the formula III $$MY \quad (III)$$

wherein

Y is halogen, $OR^1$, $OCOR^1$, $SR^1$, —SCN or —CN, and

M is H, Li, Na, K, $NR_4^2$ or $SiR_3^2$, and $R^1$ and $R^2$ are each, independently of one another, H, alkyl, aryl or cycloalkyl. If Y is an alkoxy group ($OR^1$), an alcohol ($HOR^1$, M=H) is preferably used as a cosolvent in order to provide a source of the alkoxy group (see Examples 2/4); if Y is a halogen, it is preferred either to use the corresponding acid without any salt or alcohol (HY/See Example 1) or an acid, e.g., sulfuric acid and a salt MY.

The invention relates, in particular, to a method for preparing 2,4-disubstituted 3-aminopyridine derivatives of the formula I

[Structure I shown]

in which

X is $NR^4$, O, S or $CH_2$

Y has the stated meaning, and $R^3$ and $R^4$ are each, independently of one another, H, alkyl, aryl or cycloalkyl, from the corresponding 4-substituted 3-nitropyridine of the formula II

[Structure II shown]

wherein X and $R^3$ have the stated meaning, especially to a method for preparing the compound of the formula Ia

[Structure Ia shown]

wherein $R^3$ has the stated meaning, and Hal is halogen.

Preferred embodiments of the method according to the invention are:

a) Methods in which the electrolysis is carried out at temperatures between 0° C. and the boiling temperature of the solvent used.

b) Methods in which the electrolysis is carried out potentiostatically or galvanostatically at a current density between 0.1 and 15 $A/dm^2$, preferably between 1 and 6 $A/dm^2$.

c) Methods in which in electrolysis cathodes made of copper, graphite or platinum are used.

d) Methods in which the anode solution is separated from the cathode solution by a diaphragm, preferably a diaphragm composed of a cation exchanger membrane having a fluorocarbon matrix.

e) Methods in which the cathode solution contains from 1 to 20% by weight of compound of the formula II, and from 1 to 80% by weight of acid and, if appropriate, an alcohol or a salt.

The invention further relates to a method for preparing a pyridino[3,4b]azole of the formula IV

[Structure IV shown]

wherein Y has the stated meaning, $R^5$ is H or alkyl, and X' is $NR^3$, O, S or $CHR^3$, characterized in that a 2,4-disubstituted 3-aminopyridine of the formula I is prepared according to at least one of Claims 2–7 and is reacted, in a manner known per se, with a carboxylic acid of the formula $R^5$—COOH or one of its reactive derivatives.

The kind of the alkyl-, aryl- or cycloalkyl substituents of the radicals $R^1$, $R^2$, $R^3$, $R^4$ and $R^5$ is not critical for carrying out the process according to the invention.

The 3-nitropyridine derivatives useable in the invention include, preferably, unsubstituted 3-nitropyridine, or 3-nitropyridine substituted in the 4-position, e.g., in particular, 4-amino or 4-alkylamino-3-nitropyridine.

Alkyl groups include, preferably, alkyl groups having from 1 to 10, in particular 1 to 4 C atoms. The alkyl radicals in the alkylamino groups, alkoxy groups and alkyl ester groups preferably have from 1 to 10, in particular 1 to 3 C atoms.

Preferred aryl radicals include homo- and heteroaromatic ring systems having five or six ring-atoms, in particular pyridine-, benzene- and pyrrol derivatives. Preference is given to those unsubstituted or substituted phenyl radicals which may contain, on the benzene ring, from 1 to 2 methyl, ethyl or isopropyl radicals, from 1 to 2 methoxy or ethoxy radicals, from 1 to 2 fluorine, chlorine or bromine atoms, from 1 to 2 carboxyl groups, 1 sulfonic acid, formyl, amino, hydroxyl or nitrile group. Preferred cycloalkyl radicals include cycloalkyl groups having from 5 to 8, preferably 6, C atoms.

The acidic solution of the 2-nitropyridine compound contains the acid, e.g., hydrochloric acid, sulfuric acid or methylsulfuric acid. It may further contain an electrolyte such as tetrabutylammonium hydrogen sulphate and a cosolvent such as water or dioxane. Preferred acids are hydrochloric acid or sulfuric acid. The nitropyridine compound solution to be used as the catholyte preferably contains up to 80 percent by weight of acid. The concentration of the nitro compound in the catholyte is preferably between 1 and 20 percent by weight. Any remainder up to 100 percent can be cosolvent. For example, the catholyte may be composed of from 1 to 20 percent by weight of the nitro compound, from 20 to 40 percent by weight of hydrogen chloride and from 40 to 80 percent by weight of water.

The electrosynthesis according to the invention can be carried out in a conventional electrolytic cell, in which anode compartment and cathode compartment are separated by a diaphragm, e.g., made of porous clay or a commercial ion exchanger membrane, such as in a cell of the filter press type, especially a cation exchanger membrane having a fluorocarbon matrix of the Nafion® type (Dupont, Aldrich).

The cathode is composed, e.g., of a plate of Pb, Sn, Zn, $V_2A$, Fe, Cu, Ni, Hg, Au, Ag, Pt, Pd, Ti, Al or of alloys of these metals. It may alternatively be composed of graphite or graphite-filled plastic or of a mercury pool and be employed in the form of metal meshes, spheres, fabrics or felts.

The anode may be composed of a graphite or Pb/PbO2 electrode or of activated and/or coated metal meshes, e.g., titanium. Alternatively, other anodes as known in organic electrochemistry can be used. The anolyte has a conventional composition. It is preferably composed of aqueous mineral acid, preferably hydrochloric acid or sulfuric acid.

The electrochemical reduction is carried out at temperatures up to the boiling point of the solvent, preferably up to 90° C., especially between 50° and 60° C. The catholyte can be set to the desired temperature, e.g., by heating the cathode, the cathode circuit or anode circuit or by means of the reaction heat. Cooling is similarly possible. The catholyte is expediently stirred or pumped over. In the case of the anolyte, circulation by means of the anode off-gas is often sufficient.

The electrolysis is carried out, e.g., by following the conversion of the nitro compound polarographically. The amino product formed and its by-products can be titrated.

Stirring on the cathode, such as brisk flow of the catholyte past the cathode, is advantageous.

The electrolysis can be carried out both potentiostatically and galvanostatically.

The current density is not critical in the method according to the invention, it is, e.g., from 0.1 to 50 A/dm$^2$, preferably from 1.0 to 15 A/dm$^2$, especially between 1 and 6 A/dm$^2$.

According to the method of the invention, valuable aminopyridines which could hitherto be prepared only laboriously, can be prepared particularly simply and advantageously. Thus, e.g., the intermediate product 3,4-diamino-2-chloropyridine required for pharmaceuticals formerly prepared conventionally by reduction of 4-amino-3-nitropyridine with tin(II) chloride, is now easily prepared.

The advantageous result of the method according to the invention, which comprises, inter alia, the point that tin(IV) salts do not have to be employed is surprising, given the prior art.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application P 43 33 697.3, filed Oct. 2, 1993, is hereby incorporated by reference.

EXAMPLES

Example 1

3,4-Diamino-2-chloropyridine from 4-amino-3-nitropyridine

Electrodes: Graphite

Diaphragm: Nafion® 417

Anolyte: 37% HCl, 1 l

Catholyte: 1.4 l of 37% HCl—17.5 g of 4-amino-3-nitropyridine

The electrolysis was carried out in a flow cell at approximately 60° C. It was performed galvanostatically, using a current density of 1.5 A/dm$^2$ up to 128% of the charge required. After the electrolysis had been terminated, the catholyte was drawn off and the dihydrochloride of the 2-chloro-3,4-diaminopyridine crystallized out by cooling in an ice bath and standing overnight. In total, 25.4 g of product could be isolated (92% of theory).

Example 2

3,4-Diamino-2-methoxypyridine from 4-amino-3-nitropyridine

In the apparatus described in Example 1, a solution of 400 ml of methanol, 15 ml of sulfuric acid and 17.5 g of 4-amino-3-nitropyridine was electrolyzed at approximately 50° C. and a current density of 1.5 A/dm$^2$ up to 120% of the charge required.

The methanol is then distilled off and the residue is admixed with water. After extraction with dichloromethane and conventional work-up, the product is obtained.

Example 3

3,4-Diamino-2-hydroxypyridine from 4-amino-3-nitropyridine

Catholyte: 450 ml of 25% $H_2SO_4$—20 g of 4-amino-3-nitropyridine

Anolyte: 75 ml of 25% $H_2SO_4$

Cathode: Graphite
Anode: Lead
Diaphragm: Ceramics-frit
Current Density: 50 mA/cm²
Temperature: 50° C.

The electrolysis has been terminated after 107% of the theoretically calculated charge had flown. The product of the electrolysis contained 86% of the desired product as verified by hplc.

Example 4

3,4-Diamino-2-methoxypyridine from 4-amino-3-nitropyridine

Catholyte: 450 ml of 25% H₂SO₄—10 g of 4-amino-3-nitropyridine
Anolyte: 75 ml of 25% H₂SO₄ in methanol
Cathode: Graphite
Anode: Graphite
Diaphragm: Ceramics-frit
Current Density: 10 mA/cm²
Temperature: 40° C.

The electrolysis has been terminated after 113% of the theoretically calculated charge had flown. The product of the electrolysis contained 93% of the desired product as verified by hplc.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process comprising electrolytically reducing a 3-nitropyridine compound in the presence of an acid and a nucleophilic group Y, which neuclophilic group is a halogen, OR¹, OCOR¹, SR¹, SCN or CN, in which R¹ is H, alkyl aryl or cycloalkyl, to produce a 2-Y-substituted 3-aminopyridine compound.

2. A method according to claim 1, wherein the reduction is conducted in the presence of an alcohol or a salt of formula III

MY     (III)

wherein

M is H, Li, Na, K, $N(R^2)_4$ or $Si(R^2)_3$, and

R² is H, alkyl, aryl or cycloalkyl.

3. A method according to claim 1, comprising preparing 2,4-disubstituted 3-aminopyridine compound of formula I

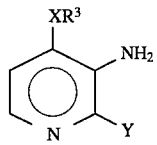 (I)

in which

X is NR⁴, O, S or CH₂

R³ and R⁴ are each, independently, H, alkyl, aryl or cycloalkyl, from a corresponding 4-substituted 3-nitropyridine of formula II

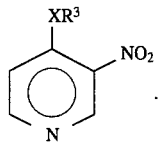 (II)

4. A method according to claim 2, comprising preparing a compound of the formula Ia

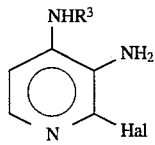 (Ia)

wherein

Hal is halogen.

5. A method according to claim 1, wherein that the electrolysis is carried out in a solvent at a temperature of 0° C. to the boiling temperature of the solvent used.

6. A method according to claim 1, wherein that the electrolysis is carried out galvanostatically or potentiostatically at a current density between 0.1 and 15 A/dm².

7. A method according to claim 1, wherein electrolysis cathodes made of copper, graphite or platinum are used.

8. A method according to claim 1, wherein anode solution is separated from cathode solution by a diaphragm.

9. A method according to claim 8, wherein the diaphragm is composed of a cation exchanger membrane having a fluorocarbon matrix.

10. A method according to claim 1, wherein the electrolysis is conducted in a cell having a cathode solution containing from 1 to 20% by weight of compound of the formula 11, and from 1 to 80% by weight of acid and, optionally, an alcohol or a salt.

11. A method according to claim 1, wherein that the electrolysis is carried out gavanostatically or potentiostatically at a current density between 2 and 4 A/dm².

12. A method according to claim 1, wherein electrolysis cathodes made of Pb, Sn, Zn, V₂A, Fe, Cu, Ni, Hg, Au, Ag, Pt, Pd, Ti, Al or an alloy thereof are used.

13. A method according to claim 1, wherein electrolysis cathodes of graphite or graphite-filled plastic are used.

14. A method according to claim 1, wherein electrolysis cathodes of metal mesh, spheres, fabric or felt are used.

15. A method according to claim 1, wherein electrolysis anodes of graphite, titanium or Pb/PbO₂ are used.

16. A process comprising electrolytically reducing a 3-nitropyridine compound in the presence of an acid and a nucleophilic group Y, which nucleophilic group is halogen, OR¹, OCOR¹, SR¹, SCN or CN, in which R¹ is H, alkyl, aryl or cycloalkyl, to produce a 2-Y-substituted 3-aminopyridine compound, wherein the electrolysis is carried out galvanostatically or potentiostatically at a current density between 0.1 and 15 A/dm² and in a solvent at a temperature of 0° C. to the boiling temperature of said solvent.

* * * * *